United States Patent

Wirth et al.

[11] Patent Number: 4,689,162
[45] Date of Patent: Aug. 25, 1987

[54] BORON-CONTAINING COMPOUNDS

[75] Inventors: Hermann O. Wirth, Bensheim; Klaus Müller, Lörrach; Hans-Helmut Friedrich, Lautertal, all of Fed. Rep. of Germany

[73] Assignee: Ciba-Geigy Corporation, Ardsley, N.Y.

[21] Appl. No.: 785,932

[22] Filed: Oct. 9, 1985

[30] Foreign Application Priority Data

Oct. 12, 1984 [CH] Switzerland ............... 4960/84

[51] Int. Cl.$^4$ ............... C10M 135/24; C10M 129/04
[52] U.S. Cl. ............... 252/32.7 E; 252/48.2; 252/48.4; 252/49.6
[58] Field of Search ............... 252/32.7 E, 49.6; 260/462 R

[56] References Cited

U.S. PATENT DOCUMENTS

| | | | |
|---|---|---|---|
| 3,303,130 | 2/1967 | Scypinski | 260/462 R |
| 4,115,286 | 9/1978 | Baldwin et al. | |
| 4,394,277 | 7/1983 | Small, Jr. | 252/32.7 E |
| 4,410,438 | 10/1983 | Horodysky | 252/49.6 |
| 4,465,605 | 8/1984 | Horodysky et al. | 252/49.6 |
| 4,530,771 | 7/1985 | Nakano et al. | 252/49.6 |
| 4,541,941 | 9/1985 | Horodyski et al. | 252/49.6 |

Primary Examiner—William R. Dixon, Jr.
Assistant Examiner—Ellen McAvoy
Attorney, Agent, or Firm—Harry Falber

[57] ABSTRACT

Compounds of the formula I

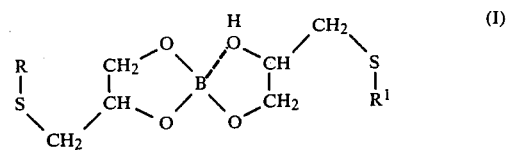

wherein R and $R^1$ are identical or different, and are cyclohexyl or a radical

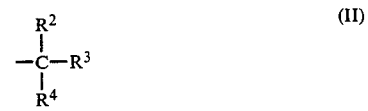

in which $R^2$ is hydrogen or $C_1$–$C_{12}$-alkyl, and $R^3$ and $R^4$ independently of one another are each $C_1$–$C_{12}$-alkyl, and the radicals $R^2$, $R^3$ and $R^4$ together contain 3–20 C atoms.

These compounds are suitable as high-pressure and anti-wear additives for lubricants and hydraulic fluids.

7 Claims, No Drawings

BORON-CONTAINING COMPOUNDS

The present invention relates to sulfur-containing boric acid derivatives, to the production thereof, and to their use as additives in lubricants and hydraulic fluids, and also to lubricants and hydraulic fluids containing these boric acid derivatives.

Additives are in general added to lubricants to improve the performance characteristics of the lubricants.

Particularly high demands are made on lubricants with regard to their load-carrying capacity for transmitting large forces. By the addition of high-pressure and anti-wear additives, the wear-phenomena otherwise occurring are greatly reduced.

Boric-acid esters of thioalkanediols are described in the U.S. patent specification No. 4,394,277 as being additives for lubricants.

The present invention relates to compounds of the formula I

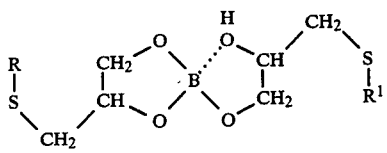

wherein R and R$^1$ are identical or different, and are cyclohexyl or a radical

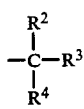

in which R$^2$ is hydrogen or C$_1$–C$_{12}$-alkyl, and R$^3$ and R$^4$ independently of one another are each C$_1$–C$_{12}$-alkyl, and the radicals R$^2$, R$^3$ and R$^4$ together contain 3–20 C atoms.

When R$^2$, R$^3$ and R$^4$ are C$_1$–C$_{12}$-alkyl, they are straight-chain or branched-chain substituents, for example methyl, ethyl, propyl, butyl, pentyl, hexyl, heptyl, octyl, nonyl, decyl, undecyl or dodecyl.

Preferably, R$^2$, R$^3$ and R$^4$ are all alkyl and together contain 3–20 C atoms, and together with the C atom to which they are bound they are for example: tert-butyl, tert-octyl, tert-nonyl and tert-dodecyl, by tert-dodecyl being meant for example a radical such as is described for tertiary dodecylmercaptan in "Ullmanns Enzyklopädie der technischen Chemie, 4th Edition, Vol. 23, p. 182, Verlag Chemie, Weinheim".

Preferred compounds of the formula I are those wherein R and R$^1$ are a group of the formula II in which R$^2$ is C$_1$–C$_{12}$-alkyl.

Particularly preferred compounds of the formula I are those wherein R and R$^1$ are a group of the formula II in which R$^2$, R$^3$ and R$^4$ together contain 3–11 C atoms.

More particularly preferred compounds of the formula I are those wherein R and R$^1$ are a group of the formula II in which R$^2$, R$^3$ and R$^4$ together contain 8 C atoms.

And quite specially preferred is the compound of the formula I wherein R and R$^1$ are tert-nonyl.

Examples of compounds of the formula I are those in which the substituents R and R$^1$ have the following meanings:

| | |
|---|---|
| R = $^t$C$_9$H$_{19}$-, R$^1$ = $^t$C$_9$H$_{19}$- | (comp. 1) |
| R = $^t$C$_{12}$H$_{25}$-, R$^1$ = $^t$C$_{12}$H$_{25}$- | (comp. 2) |
| R = $^t$C$_4$H$_9$-, R$^1$ = $^t$C$_4$H$_9$- | (comp. 3) |
| R = $^t$C$_9$H$_{19}$-, R$^1$ = $^t$C$_{12}$H$_{25}$- | (comp. 4) |
| R = $^n$C$_6$H$_{13}$-CH(CH$_3$)-, R$^1$ = $^n$C$_6$H$_{13}$-CH(CH$_3$)- | (comp. 5) |
| R = $^n$C$_{10}$H$_{21}$-CH(CH$_3$)-, R$^1$ = $^n$C$_6$H$_{13}$-CH(CH$_3$)- | (comp. 6) |
| R = cyclohexyl, R$^1$ = cyclohexyl | (comp. 7) |

The compounds of the formula I are produced in a manner known per se, using a method for example analogous to that described in the U.S. patent specification No. 4,394,277, by reaction of a sulfur-containing 1,2-alkanediol R—S—CH$_2$—CH(OH)—CH$_2$(OH) with boric acid, which results in symmetrical compounds of the formula I in which the substituents R and R$^1$ are identical. For asymmetrical compounds, the alkanediol R—S—CH$_2$—CH(OH)—CH$_2$(OH) is partially replaced by R$^1$—S—CH$_2$—CH(OH)—CH$_2$(OH).

In particular, the compounds of the formula I can be produced by reaction of an epoxide of the formula III

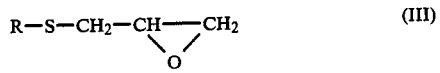

with boric acid. The reaction of approximately stoichiometric amounts (2:1) is preferred; however, a slight excess of boric acid or of the epoxide of the formula III likewise produces good results.

The reaction can be performed in a non-polar inert solvent, which is preferably immiscible with water, such as chloroform, hexane, heptane, cyclohexane or toluene. The reaction can also be carried out without solvent, the reaction medium being stirred until the boric acid disappears.

The reaction temperature is not critical; the reaction is however preferably performed at elevated temperature, especially at 80°–150° C. The procedure of carrying out the reaction at the reflux temperature of the appropriate solvent used has proved particularly favourable.

The water forming during the reaction is separated by known methods, for example by (azeotropic) distillation, by phase separation, and so forth.

The compounds of the formula I are of a thinly liquid, viscous to wax-like nature, and are surprisingly readily soluble in lubricants. They are particularly suitable as additives in lubricants, especially in motor oils, and result in an improvement of the high-pressure and anti-wear properties; reference is made also to to their anti-oxidising activity.

The compounds of the formula I are effective even in very small amounts as additives in lubricants. They are added to the lubricants in an amount of 0.01 to 5% by weight, preferably in an amount of 0.05 to 3% by weight, relative to the amount of lubricant. The lubricants concerned are familiar to a person skilled in the art, and are described for example in the "Schmiermittel Taschenbuch" [Handbook of Lubricants] (Hüthig Verlag, Heidelberg, 1974). Particularly suitable, besides mineral oils, are for example poly-α-olefins, lubricants based on esters; or phosphates, glycols, polyglycols and polyalkylene glycols. The lubricants can additionally contain other additives which are added to further improve the basic properties of lubricants: such additives include: antioxidants, metal passivators, rust inhibitors, viscosity-index improvers, pour-point depressors, dispersants, detergents, and also other high-pressure additives and anti-wear additives.

EXAMPLES OF PHENOLIC ANTIOXIDANTS 1.1. Alkylated monophenols
2,6-di-tert-butyl-4-methylphenol,
2,6-di-tert-butylphenol,
2-tert-butyl-4,6-dimethylphenol,
2,6-di-tert-butyl-4-ethylphenol,
2,6-di-tert-butyl-4-n-butylphenol,
2,6-di-tert-butyl-4-i-butylphenol,
2,6-di-cyclopentyl-4-methylphenol,
2-($\alpha$-methylcyclohexyl)-4,6-dimethylphenol,
2,6-di-octadecyl-4-methylphenol,
2,4,6-tri-cyclohexylphenol, and
2,6-di-tert-butyl-4-methoxymethylphenol.

1.2. Alkylated hydroquinones
2,6-di-tert-butyl-4-methoxyphenol,
2,5-di-tert-butyl-hydroquinone,
2,5-di-tert-amyl-hydroquinone, and
2,6-diphenyl-4-octadecyloxyphenol.

1.3. Hydroxylated thiodiphenyl ethers
2,2'-thio-bis-(6-tert-butyl-4-methylphenol),
2,2'-thio-bis-(4-octylphenol),
4,4'-thio-bis-(6-tert-butyl-3-methylphenol) and
4,4'-thio-bis-(6-tert-butyl-2-methylphenol).

1.4. Alkylidene-bisphenols
2,2'-methylene-bis-(6-tert-butyl-4-methylphenol),
2,2'-methylene-bis-(6-tert-butyl-4-ethylphenol),
2,2'-methylene-bis-[4-methyl-6-($\alpha$-methylcyclohexyl)-phenol],
2,2'-methylene-bis-(4-methyl-6-cyclohexylphenol),
2,2'-methylene-bis-(6-nonyl-4-methylphenol),
2,2'-methylene-bis-(4,6-di-tert-butylphenol),
2,2'-ethylidene-bis-(4,6-di-tert-butylphenol),
2,2'-ethylidene-bis-(6-tert-butyl-4-isobutylphenol),
2,2'-methylene-bis-[6-($\alpha$-methylbenzyl)-4-nonylphenol],
2,2'-methylene-bis-[6-($\alpha,\alpha$-dimethylbenzyl)-4-nonylphenol],
4,4'-methylene-bis-(2,6-di-tert-butylphenol),
4,4'-methylene-bis-(6-tert-butyl-2-methylphenol),
1,1-bis-(5-tert-butyl-4-hydroxy-2-methylphenyl)-butane,
2,6-di-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane,
ethylene glycol-bis-[3,3-bis-(3'-tert-butyl-4'-hydroxyphenyl)-butyrate],
di-(3-tert-butyl-4-hydroxy-5-methylphenyl)-dicyclopentadiene, and
di-[2-(3'-tert-butyl-2'-hydroxy-5'-methyl-benzyl)-6-tert-butyl-4-methyl-phenyl]-terephthalate.

1.5. Benzyl compounds
1,3,5-tri-(3,5-di-tert-butyl-4-hydroxybenzyl)-2,4,6-trimethylbenzene,
di-(3,5-di-tert-butyl-4-hydroxybenzyl)-sulfide,
3,5-di-tert-butyl-4-hydroxybenzyl-mercaptoacetic acid isooctyl ester,
bis-(4-tert-butyl-3-hydroxy-2,6-dimethylbenzyl)dithiol-terephthalete,
1,3,5-tris-(3,5-di-tert-butyl-4-hydroxybenzyl)-isocyanurate,
1,3,5-tris-(4-tert-butyl-3-hydroxy-2,6-dimethylbenzyl)isocyanurate,
3,5-di-tert-butyl-4-hydroxybenzylphosphonic acid dioctadecyl ester, and
calcium salt of 3,5-di-tert-butyl-4-hydroxybenzylphosphonic acid monoethyl ester.

1.6. Acylaminophenols
4-hydroxylauric acid anilide,
4-hydroxystearic acid anilide,
2,4-bis-octylmercapto-6-(3,5-di-tert-butyl-4-hydroxyanilino)-s-triazine, and
N-(3,5-di-tert-butyl-4-hydroxyphenyl)-carbamic acid octyl ester.

1.7. Esters of $\beta$-(3,5-di-tert-butyl-4-hydroxyphenyl)-propionic acid with monohydric or polyhydric alcohols, for example with:
methanol, octadecanol, 1,6-hexanediol, neopentyl glycol, thiodiethylene glycol, diethylene glycol, triethylene glycol, pentaerythritol, tris-hydroxyethyl isocyanurate, and
di-hydroxyethyloxalic acid diamide.

1.8. Esters of $\beta$-(5-tert-butyl-4-hydroxy-3-methylphenyl)propionic acid with monohydric or polyhydric alcohols, for example with:
methanol, octadecanol, 1,6-hexanediol, neopentyl glycol, thiodiethylene glycol, diethylene glycol, triethylene glycol, pentaerythritol, tris-hydroxyethyl isocyanurate, and di-hydroxyethyloxalic acid diamide.

1.9. Amides of $\beta$-(3,5-di-tert-butyl-4-hydroxyphenyl)-propionic acid with for example:
N,N'-di-(3,5-di-tert-butyl-4-hydroxyphenylpropionyl)-hexamethylenediamine,
N,N'-di-(3,5-di-tert-butyl-4-hydroxyphenylpropionyl)-trimethylenediamine, and
N,N'-di-(3,5-di-tert-butyl-4-hydroxyphenylpropionyl)-hydrazine.

EXAMPLES OF AMINE ANTIOXIDANTS

N,N'-diisopropyl-p-phenylenediamine,
N,N'-di-sec-butyl-p-phenylenediamine,
N,N'-bis(1,4-dimethylpentyl)-p-phenylenediamine,
N,N'-bis(1-ethyl-3-methylpentyl)-p-phenylenediamine,
N,N'-bis(1-methylheptyl)-p-phenylenediamine,
N,N'-diphenyl-p-phenylenediamine,
N,N'-di-(naphthyl-2-)-p-phenylenediamine,
N-isopropyl-N'-phenyl-p-phenylenediamine,
N-(1,3-dimethylbutyl)-N'-phenyl-p-phenylenediamine,
N-(1-methylheptyl)-N'-phenyl-p-phenylenediamine,
N-cyclohexyl-N'-phenyl-p-phenylenediamine,
4-(p-toluenesulfonamido)-diphenylamine,
N,N'-dimethyl-N,N'-di-sec-butyl-p-phenylenediamine,
diphenylamine,
4-isopropoxydiphenylamine,
4-phenyl-1-naphthylamine,
N-phenyl-2-naphthylamine,
octylated diphenylamine,
4-n-butylaminophenol,
4-butyrylaminophenol,
4-nonanoylaminophenol,
4-dodecanoylaminophenol,
4-octadecanoylaminophenol,
di-(4-methoxyphenyl)-amine,
2,6-di-tert-butyl-4-dimethylaminomethylphenol,
2,4'-diaminodiphenylmethane,
4,4'-diaminodiphenylmethane,
N,N,N',N'-tetramethyl-4,4'-diaminodiphenylmethane,
1,2-di-[(2-methylphenyl)-amino]-ethane,
1,2-di-(phenylamino)-propane (o-tolyl)-biguanide,
di-[4-(1′,3′-dimethylbutyl)-phenyl)]amine,
tert-octylated N-phenyl-1-naphthylamine, and
mixture of mono- and dialkylated tert-butyl/tert-octyl-diphenylamines.

Examples of metal passivators are:

for copper, for example: benzotriazole, tetrahydrobenzotriazole, 2-mercaptobenzothiazole, 2,5-dimercaptothiadiazole, salicylidene-propylenediamine and salts of salicylaminoguanidene.

Examples of rust inhibitors are:

(a) organic acids, the esters thereof, metal salts and anhydrides thereof, for example: N-oleoylsarcosine, sorbitan monooleate, lead naphthenate, dodecenylsuccinic acid anhydride, alkenylsuccinic acid half-ester and 4-nonylphenoxyacetic acid;

(b) nitrogen-containing compounds, for example

I. primary, secondary or tertiary aliphatic or cycloaliphatic amines and amine salts of organic and inorganic acids, for example oil-soluble alkylammoniumcarboxylates;

II. heterocyclic compounds, for example: substituted imidazolines and oxazolines;

(c) phosphorus-containing compounds, for example: amine salts of phosphoric acid partial esters;

(d) sulfur-containing compounds, for example: barium dinonylnaphthalenesulfonates and calcium petroleum sulfonates.

Examples of viscosity-index improvers are for example:

polymethacrylate, vinyl pyrrolidone/methacrylate copolymers, polybutenes, olefin copolymers and styrene/acrylate copolymers.

Examples of pour-point depressors are for example:

polymethacrylate and alkylated naphthalene derivatives.

Examples of dispersants/surfactants are for example:

polybutenylsuccinimides, polybutenylphosphonic acid derivatives, basic magnesium, calcium and barium sulfonates and phenolates.

Examples of high-pressure and/or anti-wear additives are for example:

compounds containing sulfur and/or phosphorus and/or halogen, such as sulfurised vegetable oils, zinc dialkyldithiophosphates, tritolylphosphate, chlorinated paraffins and alkyl- and aryldisulfides.

EXAMPLE 1 (COMPOUND 1)

260 g (1.2 mols) of $^tC_9H_{19}$-glycidyl thioether (for producing this there is used $^tC_9H_{19}SH$ ex Phillips Petroleum Co.), 34 g (0.55 mol) of boric acid and 450 ml of toluene are combined in a 1 1 three-necked flask fitted with a water-separator and, with stirring under refluxing conditions, the reaction water is azeotropically removed. After filtration has been performed, the toluene is removed by means of a rotary evaporator.

Yield: 281 g; colourless liquid; $n_D^{20} = 1.4990$.

An acid titration based on the Boeseken complex gives a content of 93%.

EXAMPLE 2 (COMPOUND 2)

The reaction of $^tC_{12}H_{25}$-glycidyl thioether is performed in an analogous manner:
colourless viscous liquid; $n_D^{20} = 1.4952$.

EXAMPLE 3 (COMPOUND 1)

6.2 g (0.1 mol) of boric acid, 47.0 g (0.2 mol) of $^tC_9H_{19}$-glycerol monothioether and 150 ml of toluene are placed into a 250 ml three-necked flask, and the reaction water is removed azeotropically whilst stirring under refluxing conditions is maintained. The reaction mixture is then concentrated with the aid of a rotary evaporator, and finally by means of a vacuum pump.

Yield: 48.8 g; colourless viscous liquid; $n_D^{20} = 1.4965$.

The further structure is established by $^{11}$B-NMR.

EXAMPLE 4 (COMPOUND 2)

The reaction of $^tC_{12}H_{25}$-glycerol monothioether is performed in an analogous manner;
colourless liquid; $n_D^{20}$: 14950.

EXAMPLE 5: Testing of the load-carrying capacity (FGZ test according to DIN 51,354).

A mineral oil ISO VG 32 is used as the test fluid to determine the effectiveness of the additives.

The values obtained are summarised in Table 1.

TABLE 1

| Additive Example No. | Conc. of additive % | Damage-load stage |
|---|---|---|
| 1 | 0.25 | 10 |
| 2 | 0.25 | 10 |
| control | — | 5–6 |

What is claimed is:

1. A compound of the formula I

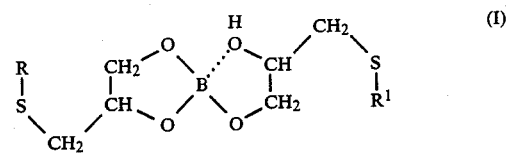

wherein R and $R^1$ are identical or different, and are cyclohexyl or a radical

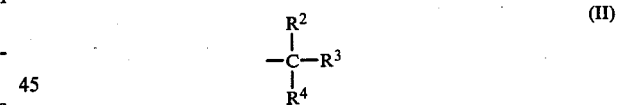

in which $R^2$ is hydrogen or $C_1$–$C_{12}$-alkyl, and $R^3$ and $R^4$ independently of one another are each $C_1$–$C_{12}$-alkyl, and the radicals $R^2$, $R^3$ and $R^4$ together contain 3–20 C atoms.

2. A compound according to claim 1 of the formula I wherein R and $R^1$ are a group of the formula II in which $R^2$ is $C_1$–$C_{12}$-alkyl.

3. A compound according to claim 1 of the formula I wherein R and $R^1$ are a group of the formula II in which $R^2$, $R^3$ and $R^4$ together contain 3–11 C atoms.

4. A compound according to claim 3, wherein $R^2$, $R^3$ and $R^4$ together contain 8 C atoms.

5. A compound according to claim 1 of the formula I wherein R and $R^1$ are tert-nonyl.

6. A lubricant containing a compound of the formula I according to claim 1.

7. A method for improving the performance characteristics of lubricants which comprises incorporating into said lubricants an effective performance improving amount of a compound of the formula I according to claim 1.

* * * * *